US006410815B1

(12) United States Patent
Plee et al.

(10) Patent No.: US 6,410,815 B1
(45) Date of Patent: Jun. 25, 2002

(54) AGGLOMERATED ZEOLITE ADSORBENTS, PROCESS FOR THEIR PREPARATION, AND THEIR USE FOR ADSORBING PARAXYLENE FROM AROMATIC $C_8$ FRACTIONS

(75) Inventors: Dominique Plee, Puteaux; Alain Methivier, Rueil-Malmaison, both of (FR)

(73) Assignee: Elf Atochem S.A., Puteaux (FR)

( * ) Notice: Subject to any disclaimer, the term of this patent is extended or adjusted under 35 U.S.C. 154(b) by 0 days.

(21) Appl. No.: 09/485,907

(22) PCT Filed: Aug. 18, 1998

(86) PCT No.: PCT/FR98/01818

§ 371 (c)(1),
(2), (4) Date: May 10, 2000

(87) PCT Pub. No.: WO99/10096

PCT Pub. Date: Mar. 4, 1999

(30) Foreign Application Priority Data

Aug. 21, 1997 (FR) .............................. 97 10535

(51) Int. Cl.⁷ .............................. C07C 7/00; C07C 7/12; B01J 29/06; B01J 29/08; B01J 21/16
(52) U.S. Cl. ...................... 585/828; 585/804; 585/805; 585/825; 585/831; 585/829; 502/63; 502/64; 502/68; 502/79; 502/84
(58) Field of Search .................... 585/829, 804, 585/805, 825, 828, 831; 502/63, 64, 68, 79, 84

(56) References Cited

U.S. PATENT DOCUMENTS

| 2,882,244 A | 4/1959 | Milton ........................ 252/455 |
| 2,985,589 A | 5/1961 | Broughton et al. ........... 210/34 |
| 3,130,007 A | 4/1964 | Breck .......................... 23/113 |
| 3,558,730 A | 1/1971 | Neuzil ........................ 260/674 |
| 3,558,732 A | 1/1971 | Neuzil ........................ 260/674 |
| 3,626,020 A | 12/1971 | Neuzil ........................ 260/674 |
| 3,663,638 A | 5/1972 | Neuzil ........................ 260/674 |
| 3,878,127 A | 4/1975 | Rosback ..................... 252/455 |
| 5,629,467 A | 5/1997 | Hotier et al. ................ 585/805 |

FOREIGN PATENT DOCUMENTS

| DE | 296002 | * 11/1991 | |
| EP | 0 531 191 A1 | 8/1992 | ..................... 15/8 |

OTHER PUBLICATIONS

Julius Grant "Hackh's Chemical Dictionary" Fourth edition, p. 369.*

* cited by examiner

Primary Examiner—Walter D. Griffin
Assistant Examiner—Tam M. Nguyen
(74) Attorney, Agent, or Firm—Smith, Gambrell & Russell, LLP

(57) ABSTRACT

The present invention relates to agglomerated zeolite adsorbents based on faujasite with an Si/Al ratio such that $1 \leq Si/Al \leq 1.15$, at least 70% exchanged with barium and optionally with potassium, and on a binder, preferably a zeolitizable binder.

They are obtained by agglomerating zeolite powder with a binder, followed by exchange of the zeolite ions for barium ions and activation of the adsorbents thus exchanged.

These adsorbents are particularly suitable for the adsorption of the para-xylene contained in aromatic $C_8$ hydrocarbon fractions in the liquid phase, in processes of simulated fluid-bed type.

16 Claims, No Drawings

AGGLOMERATED ZEOLITE ADSORBENTS, PROCESS FOR THEIR PREPARATION, AND THEIR USE FOR ADSORBING PARAXYLENE FROM AROMATIC C₈ FRACTIONS

TECHNICAL FIELD

The field of the invention is that of zeolite adsorbents for the separation of xylenes, in particular with a view to the industrial production of para-xylene.

BACKGROUND ART

High-purity para-xylene is reclaimed industrially, inter alia, in order to be converted into terephthalic acid intended for the manufacture of PET.

The prior art has recognized that adsorbents consisting of zeolites X or Y exchanged using ions such as barium, potassium or strontium, alone or as a mixture, are efficient at selectively adsorbing para-xylene in a mixture containing at least one other aromatic $C_8$ isomer. U.S. Pat. Nos. 3,558,730, 3,558,732, 3,626,020 and 3,663,638 disclose adsorbents comprising aluminosilicates exchanged with barium and potassium, which efficiently separate para-xylene from a mixture of aromatic $C_8$ isomers. These adsorbents are used as adsorption agents in liquid-phase processes, preferably of the simulated counter-current type similar to those described in U.S Pat. No. 2,985,589, which are applied, inter alia, to the aromatic $C_8$ fractions derived, for example, from processes for the dialkylation of benzene, in gas-phase processes.

The performance of the industrial process for the separation of para-xylene depends largely on the adsorbent, on its adsorbing capacity and on the selectivity which it shows-for para-xylene in a medium consisting of $C_8$ aromatics, typically para-xylene itself (PX), meta-xylene (MX), ortho-xylene (OX) and ethylbenzene (EB), as well as on the ability of desorbents, such as toluene and para-diethylbenzene, to desorb the adsorbed para-xylene therefrom.

The selectivity Sel(B/A) of the adsorbent for a compound (B) relative to a compound (A) is defined as the ratio of the concentrations of the compounds in the adsorbed phase divided by the ratio of concentrations of the compounds in the non-adsorbed phase at equilibrium.

The selectivity equation is as follows:

$$\mathrm{Sel}(B/A) = \frac{(B)z/(A)z}{(B)s/(A)s}$$

where (B)z and (B)s represent the concentrations of B in the zeolite and in the solution, respectively, where (A)z and (A)s represent the concentrations of A in the zeolite and in the solution. The method for evaluating these magnitudes is outlined later.

The zeolites encountered in the prior art for the separation of xylenes belong to the faujasite structural type, first described in U.S Pat. No. 2,882,244 and U.S Pat. No. 3,130,007, which are crystalline silicoaluminates having cages of fully defined size connected three-dimensionally. The faujasites correspond to the general formula:

(1±1) $M_{2/n}O$ ; $Al_2O_3$; W $SiO_2$; Y $H_2O$ in which

M represents at least one alkali metal cation or alkaline-earth metal cation of valency n, Y is less than or equal to 8 depending on the nature of M and the degree of hydration of the crystal, W is the factor which makes it possible to distinguish between silica-rich faujasites (faujasites Y) and alumina-rich faujasites (faujasites X).

Faujasites X should be placed in the range W≦3, and faujasites Y in the range W>3, which is interpreted, rather, according to the Si/Al ratio on either side of 1.5. For the purposes of the present invention, an additional convenient distinction is introduced with faujasites with a low silica content (which will be referred to by the abbreviation LSX used by those skilled in the art, meaning Low Silica X), for W<2.3 (Si/Al<1.15).

The prior art has recognized, as adsorbent for the separation of xylenes, only those faujasites exchanged with barium with Si/Al atomic ratios of between 1.2 and 2.6. In this matter, a person skilled in the art does not appear to have available any simple and sufficiently reliable criterion for predicting their behaviour. Thus, the search for increasingly improved adsorbents proceeds by more or less random research, such as, for example, the result disclosed and claimed by U.S Pat. No. 3,878,127 with an actual barium exchange of zeolite X pretreated with a sodium hydroxide solution. The Applicant proposes adsorbents which offer para-xylene/meta-xylene or para-xylene/ortho-xylene selectivities of at least 2.0 and, advantageously, of at least 2.5, measured according to the test described in the examples. The invention achieves this result, with a number of advantages which will become apparent in the description.

DISCLOSURE OF INVENTION

The subject of the present invention is agglomerated zeolite adsorbents comprising at least 70% and preferably at least 80% of faujasite with an Si/Al atomic ratio such that 1≦Si/Al≦1.15, in which the exchangeable sites are at least 70% occupied by barium ions and optionally up to 30% by potassium (any remainder generally being made up of alkali metal ions or alkaline-earth metal ions other than barium and potassium) and agglomerated with a binder, the preferred faujasites being those in which the overall level of exchange for barium alone or for barium+potassium is greater than or equal to 90%.

One process for the preparation of the agglomerated zeolite adsorbents according to the invention consists, firstly, in agglomerating zeolite powder with an Si/Al ratio such that 1≦Si/Al≦1.15 with a binder, preferably a zeolitizable binder.

The term agglomeration is understood to refer to the production of solid particles from a mixture of zeolite(s) and binder(s) using any technique known to those skilled in the art, such as extrusion, granulation, compacting or spraying. The practical content of binder in the agglomerate generally does not exceed 30%, and preferably 20%, of the total mass of the adsorbent. The efficiency of these adsorbents is improved substantially by selecting a clay of the kaolin family as agglomeration binder, in practice kaolinite or halloysite, and by subjecting the granules to zeolitization.

Zeolitization of the binder is performed by immersing the agglomerate in an alkaline liquor, sodium hydroxide or a mixture of sodium hydroxide and potassium hydroxide whose concentration is preferably at least 0.5 M, after the grains have been calcined, the first result of this first calcination being to harden the grain, but also to activate the clay by converting it into meta-kaolin. The zeolitization is preferably carried out under hot conditions since working at the higher temperature improves the kinetics of the process and reduces the immersion times. Zeolitizations of at least 50% of the binder, that is to say that the resulting adsorbent generally consists of at least 85% and preferably at least 90% zeolite of active faujasite type and of not more than 15%, preferably not more than 10% of material which is inactive for the adsorption, are thus readily obtained.

The barium exchange is performed in an entirely conventional manner, preferably by successive exchanges so as to reach a minimum target exchange level of at least 70% and preferably at least 90%.

The potassium exchange can be performed before or after the barium exchange, but it is also possible to agglomerate faujasite LSX powder already containing potassium ions.

The activation is the final step in the production of the adsorbents of the invention. Its aim is to fix the water content, more simply the loss on ignition of the adsorbent, within optimal limits. The most practical way of proceeding is by thermal activation, which is preferably carried out between 180 and 250° C.

The invention also consists of an improvement to the process for recovering para-xylene from aromatic $C_8$ isomer fractions, which consists in using, as adsorption agent, a zeolite adsorbent based on faujasite with an Si/Al ratio such that $1 \leq Si/Al \leq 1.15$, in which the exchangeable sites are at least 70% occupied by barium ions (the remainder being made up of alkali metal ions or alkaline-earth metal ions other than barium) agglomerated with a binder, preferably a zeolitizable binder. The agglomerated zeolite adsorbents according to the invention are suitable when they are used in processes in the liquid phase or in the gas phase.

The desired product can thus be separated out by preparative adsorption liquid chromatography (batchwise), advantageously in a simulated fluid bed, i.e. one with a simulated counter-current or a simulated co-current, and more particularly with a simulated counter-current.

The operating conditions of an industrial unit for adsorption of simulated counter-current type are generally as follows:

| Number of beds | 6 to 30 |
| Number of zones | at least 4 |
| Temperature | 100 to 250° C., preferably 150 to 190° C. |
| Pressure | 0.2 to 3 MPa |
| Flow rates of desorbent to feedstock | 1 to 2.5 |

(for example 1.4 to 1.8 for an adsorption unit alone (stand-alone) and 1.1 to 1.4 for an adsorption unit combined with a crystallization unit)

| Level of recycling | 3.5 to 12, preferably 4 to 6 |

Reference may be made to U.S. Pat. Nos. 2,985,589, 5,284,992 and 5,629,467.

The operating conditions for a simulated co-current adsorption industrial unit are generally the same as those operating in simulated counter-current, except for the level of recycling, which is generally between 0.8 and 7. Reference may be made to U.S Pat. Nos. 4,402,832 and 4,498,991.

The desorption solvent can be a desorbent whose boiling point is less than that of the feedstock such as toluene, but also a desorbent whose boiling point is greater than that of the feedstock, such as para-diethylbenzene (PDEB).

Faujasites with an Si/Al ratio more or less equal to 1, which are prepared according to the production method described in European patent EP 486,384 or U.S Pat. No. 5,173,462, are preferred here. The selectivity of the adsorbents according to the invention for the adsorption of the p-xylene contained in $C_8$ aromatic fractions is optimal when their loss on ignition, measured at 900° C., is generally between 4.0 and 7.7%, and preferably between 5.2 and 7.7%. Water and a small amount of carbon dioxide form part of the loss on ignition.

The non-limiting examples which follow will allow the invention to be understood more clearly.

EXAMPLES

These examples involve the measurement or evaluation of certain characteristic magnitudes of the adsorbents of the invention.

In order to evaluate the selectivity afforded by the adsorbent in a process for the separation of para-xylene, it is subjected to a test which makes it possible to measure its separating power between para-xylene (PX) and the aromatic $C_8$ isomers thereof (MX, OX), but also between para-xylene and ethylbenzene (EB), which is important since certain fractions can be rich in ethylbenzene and not in other $C_8$ isomers, and also between para-xylene and the desorbent, since it is just as important to have available a low PX/desorbent selectivity, which is the condition for the desorption to be effective.

The test consists in immersing an adsorbent (17 grams), thermally preactivated and cooled in the absence of air, in 80 g of a mixture of aromatics dissolved in 2,2,4-trimethylpentane.

The exact composition of the mixture is as follows:

| PX | 2% |
| MX | 2% |
| OX | 2% |
| EB | 2% |
| desorbent (toluene or p-diethylbenzene) | 2% |
| 2,2,4-trimethylpentane | remainder |

The mixture is autoclaved at 150° C. for 4 hours, which is long enough to ensure that the adsorption reaches equilibrium. Some of the liquid is then removed, condensed at −30° C. and analysed by gas chromatography. It is then possible to return to the concentrations in the adsorbed phase and in the non-adsorbed phase and to express the amount of para-xylene adsorbed and the selectivities for para-xylene relative to the other aromatics and to the desorbent. The 2,2,4-trimethylpentane does not disrupt these results since it is adsorbed very little.

For Examples 1 to 9, the desorbent used is toluene, and paradiethylbenzene for Example 10.

Example 1

Preparation of a Control Adsorbent

An industrial zeolite NaX, with an Si/Al ratio=1.25 and an Na/Al ratio=1, is agglomerated by intimately mixing 850 grams of zeolite X powder (expressed as calcined equivalent), 150 grams of Charentes kaolinite (expressed as calcined equivalent) and 6 grams of carboxymethylcellulose (retention adjuvant intended to retain the water during the extrusion operation) with the appropriate amount of water for the extrusion. The extrudate is dried, crushed so as to recover grains whose equivalent diameter is equal to 0.7 mm, and then calcined at 550° C. under a stream of nitrogen for 2 hours. Its toluene-adsorbing capacity, determined at 25° C. and under a partial pressure of 0.5, is 20.2%; this is interpreted as a micropore volume of 20.2/0.86=0.235 cm³/g (in calculating the pore volume, it is considered that the density of the liquid phase is identical to the density of the adsorbed toluene, i.e. 0.86). This granule is exchanged using a 0.5 M/l barium chloride solution at 95° C. in 4 steps. At each step, the ratio by volume of solution to the mass of solid is 20 ml/g and the exchange is continued for 4 hours each time. Between each exchange, the solid is washed several times in order to free it of the excess salt. It is then activated at a temperature of 250° C. for 2 hours under a stream of nitrogen. Its toluene-adsorbing capacity is 14.8%, which equates to a micropore volume of 0.17 cm³/g. The loss on ignition is also measured, which is an important magnitude since it gives an estimate of the residual water present on the adsorbent: a loss on ignition of 4.5% is found here.

Application of the selectivity test leads to the following results:

| Isomers | Selectivity |
| --- | --- |
| PX/OX | 2.25 |
| PX/MX | 2.12 |
| PX/EB | 1.77 |
| PX/Tol | 1.52 |

The amount of para-xylene adsorbed is equal to 0.054 cm³/g

The effective zeolite content in this adsorbent is close to 85%

Example 2

Preparation of an Adsorbent According to the Invention 950 grams (calcined equivalent) of a zeolite X with an Si/Al ratio=1.01 obtained according to the process described in European Patent EP 0,486,384 or U.S. Pat. No. 5,173,462, are agglomerated with 170 grams (calcined equivalent) of Charentes kaolinite, 6 grams of carboxymethylcellulose and the appropriate amount of water to correctly extrude the paste obtained. The extrudates are then dried, after which they are calcined at a temperature of 600° C. for 2 hours under a stream of dry nitrogen. They are then crushed in order to bring the equivalent diameter of the particles to 0.7 mm.

The crushed material thus obtained is subjected to the barium exchange treatment already described in Example 1 and is heat-activated at a temperature of 220° C. The product thus obtained has a loss on ignition of 5% and a toluene-adsorbing capacity of 13% (0.15 cm³/g micropore volume).

The adsorbent satisfies the selectivity test with the following values:

| Isomers | Selectivity |
| --- | --- |
| PX/OX | 2.60 |
| PX/MX | 2.55 |
| PX/EB | 2.80 |
| PX/Tol | 2.00 |

The amount of para-xylene adsorbed during the test is 0.057 cm³/g, i.e. the same as that measured on the adsorbent of Example 1 despite the difference in micropore volume. Better selectivity towards ethylbenzene is also noted, which may be advantageous when loads rich in this isomer need to be treated. The value for the selectivity of para-xylene with respect to toluene is entirely favourable to desorption of the para-xylene by means of a reasonable consumption of desorbent.

Example 3

Preparation of an Adsorbent According to the Invention

As above, 950 grams of a zeolite X with an Si/Al ratio=1.01 are agglomerated with 170 grams of Charentes kaolinite, 6 grams of carboxymethylcellulose and the appropriate amount of water. The mixture is extruded. The extrudates are dried, calcined at a temperature of 600° C. for 2 hours under a stream of dry nitrogen and are then crushed so as to bring their equivalent diameter to 0.7 mm.

10 grams of these agglomerates are then immersed in 17 ml of a 220 g/l sodium hydroxide solution for 3 hours at 95° C. They are then washed four times with water.

In order to estimate the effectiveness of the zeolitization, a small portion of the product is heated to 550° C. under a stream of dry nitrogen and a toluene-adsorbing capacity of 21.6% is determined. The overall active zeolite content is estimated at 95%, i.e. greater than its initial content in the agglomerated adsorbent.

The solid is then exchanged with barium under the same conditions as those outlined in Example 1. After activation under dry nitrogen at 220° C. for 2 hours, a toluene-adsorbing capacity of 15% (micropore volume: 0.175 cm³/g) and a loss on ignition of 5.2% are measured.

The adsorbent thus prepared is evaluated by the selectivity test.

The following are obtained:

| Isomers | Selectivity |
| --- | --- |
| PX/OX | 2.64 |
| OX/MX | 2.60 |
| PX/EB | 2.75 |
| PX/Tol | 1.94 |

The amount of para-xylene adsorbed during the test is equal to 0.066 cm³/g. The selectivities with respect to the various isomers compare favourably with that of the adsorbent of Example 2, which reflects that the active element of the two products is a zeolite LSX. The substantial gain in para-xylene absorbed is the consequence of the richness in LSX on account of the zeolitization of the binder.

Examples 4 to 7

Preparation and Test of Adsorbents According to the Invention Which Have Undergone Various final Calcinations The sample preparation is repeated as in Example 3, the only difference being that the activation temperature was varied between 180° and 300° C.: 180° C. for Example 4, 200° C. for Example 5, 220° C. (Example 3 repeated), 250° C. for Example 6 and 300° C. for Example 7.

The compared characteristics of these products are given in the table below.

| Examples | 4 | 5 | 3 | 6 | 7 |
|---|---|---|---|---|---|
| Activation temperature (° C.) | 180 | 200 | 220 | 250 | 300 |
| Microporosity | 0.132 | 0.17 | 0.175 | 0.178 | 0.185 |
| Para-xylene adsorbed | 0.0506 | 0.065 | 0.066 | 0.062 | 0.051 |
| PX/OX | 2.91 | 4.21 | 2.64 | 2.17 | 1.45 |
| PX/MX | 3.06 | 3.11 | 2.60 | 2.01 | 1.55 |
| PX/EB | 2.00 | 2.37 | 2.75 | 2.76 | 2.34 |
| PX/Tol | 2.28 | 1.55 | 1.94 | 1.90 | 1.19 |
| Loss on ignition (%) | 7.7 | 6.6 | 5.2 | 4.4 | 2.4 |

The preferred PX/OX and PX/MX target selectivity of at least 2.5 is satisfied for these zeolites when the loss on ignition (roughly speaking, the water content) measured after the step of activation of the exchanged product is from 5.2 to 7.7%, which is achieved in practice by heat-activation at a temperature of between 180 and 220° C.

The preferred PX/EB target selectivity of at least 2.5 is satisfied for these zeolites when the loss on ignition (roughly speaking, the water content) is from 4.4 to 5.2%, which is achieved in practice by heat-activation at a temperature of between 220 and 250° C.

The activation at 250° C. has a mildly adverse effect on these performance levels but the product nevertheless remains advantageous for treating fractions that are relatively rich in ethylbenzene.

Example 8

Agglomerated samples are prepared as indicated in Example 3, which are exchanged with potassium and then according to the procedure below:

A rigorous potassium exchange is performed on an agglomerate whose binder has been zeolitized, using 1M KCl solution at 25° C. in four successive steps. At each step, the volume of solution/mass of solid ratio is 20 ml/g and the exchange is continued for 4 hours each time. Between each exchange, the solid is washed several times so as to free it of the excess salt. The product obtained has a potassium exchange level of 97.5%. It is then subjected to 2 barium exchange operations identical to those described in Example 1. After all of these operations, the solid is finally activated at a temperature of 200° C. for 2 hours under a stream of nitrogen. It has the following characteristics:

| Barium exchange level | 74.3% |
|---|---|
| Potassium exchange level | 24% |
| Toluene-adsorption capacity | 15% |
| Micropore volume | 0.174 cm³/g |
| Loss on ignition at 900° C. | 6.4% |

The adsorbent thus prepared satisfies the 25 selectivity test with the following values:

| Isomers | Selectivity |
|---|---|
| PX/OX | 3.82 |
| PX/MX | 3.01 |
| PX/EB | 2.42 |
| PX/Tol | 1.72 |

The amount of para-xylene adsorbed during the test is 0.06 cm³/g.

Example 9

950 grams (calcined equivalent) of a zeolite X with an Si/Al ratio=1.12, whose synthesis is inspired from "Investigation on the crystallization of X-type zeolites" by H. Lechert, Zeolites, 1991, Vol. 11, pp. 720–728, are agglomerated with 170 grams (calcined equivalent) of kaolinite from Charentes, 6 grams of carboxymethylcellulose and a suitable amount of water to allow the paste obtained to be extruded correctly. The extrudates are subsequently dried and then calcined at a temperature of 600° C. for 2 hours under a stream of dry nitrogen. Crushing is then carried out so as to bring the equivalent diameter of the particles to 0.7 mm.

The crushed material thus obtained is subjected to the barium exchange treatment described in Example 1 and heat-activated at a temperature of 220° C. for 2 hours. The product thus obtained has a loss on ignition of 5.2% and a toluene-adsorption capacity of 13.7% (0.159 cm³/g micropore volume).

The adsorbent satisfies the selectivity test with the following values:

| Isomers | Selectivity |
|---|---|
| PX/OX | 2.52 |
| PX/MX | 2.50 |
| PX/EB | 2.62 |
| PX/Tol | 1.78 |

The amount of para-xylene adsorbed during the test is 0.059 cm³/g.

Example 10

The adsorbent prepared in Example 3 is subjected to an identical selectivity test using para-diethylbenzene as desorbent, and the following values are found:

| Isomers | Selectivity |
|---|---|
| PX/OX | 2.65 |
| PX/MX | 2.58 |
| PX/EB | 2.70 |
| PX/PDEB | 1.12 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

What is claimed is:

1. Agglomerated zeolite adsorbents comprising at least 70% of faujasite with an Si/Al atomic ratio such that $1 \leq Si/Al \leq 1.15$, in which exchangeable sites of the zeolite adsorbents are at least 70% occupied by barium ions, and optionally up to 30% occupied by potassium, and in which the zeolite adsorbents are agglomerated with a binder, wherein the adsorbents have a loss on ignition, measured at 900° C., of between 4.0 and 7.7%.

2. Adsorbents according to claim 1, wherein the binder is a zeolitizable binder.

3. Adsorbents according to claim 1, wherein an overall level of exchange for barium alone, or for barium and potassium, is greater than or equal to 90%.

4. Process for obtaining the adsorbents defined in claim 1, comprising the following steps:
   a) agglomerating zeolite powder with a binder,
   b) calcining the agglomerate,
   c) optional zeolitization of the binder by immersing the agglomerate in an alkaline liquor, sodium hydroxide or a mixture of sodium hydroxide and potassium hydroxide,
   d) exchanging the exchangeable sites with barium, and optionally with potassium, and
   e) activating the adsorbents.

5. Process for obtaining adsorbents according to claim 4, wherein the activation in step e) is a thermal activation performed at a temperature of 180 to 250° C.

6. Process for obtaining the adsorbents according to claim 4, wherein the alkaline solution in step c) has a concentration of at least 0.5 M.

7. Process for the recovery of para-xylene from aromatic $C_8$ isomer fractions in a liquid phase, comprising adsorbing the para-xylene using the adsorbents according to claim 1 in the presence of a desorbent.

8. Process for the recovery of para-xylene according to claim 7, wherein the adsorbing occurs in a simulated fluid-bed.

9. Process for the recovery of para-xylene according to claim 8, wherein the adsorbing occurs in a simulated counter-current.

10. Process for the recovery of para-xylene according to claim 8, wherein the adsorbing occurs in a simulated co-current.

11. Process for the recovery of para-xylene from aromatic $C_8$ isomer fractions in a gaseous phase, comprising adsorbing the para-xylene using the adsorbents according to claim 1 in the presence of a desorbent.

12. Process for the recovery of para-xylene according to claim 7, wherein the desorbent is toluene or para-diethylbenzene.

13. The adsorbents according to claim 1, wherein the agglomerated zeolite adsorbents comprise at least 80% of faujasite.

14. The adsorbents according to claim 2, wherein the binder is a clay of kaolin.

15. The adsorbents according to claim 14, wherein the binder is kaolinite or halloysite.

16. The adsorbents according to claim 1, wherein the loss on ignition is between 5.2 and 7.7%.

* * * * *